(12) United States Patent
Sha et al.

(10) Patent No.: US 7,738,943 B2
(45) Date of Patent: Jun. 15, 2010

(54) SYSTEM AND METHOD FOR IDENTIFYING PERIODIC MOTION COMPLEXES FOR MR IMAGING TRIGGERING

(75) Inventors: Liewei Sha, Waukesha, WI (US); Sanjay G. Mathias, Waukesha, WI (US); Louis M. Frigo, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1039 days.

(21) Appl. No.: 10/904,629

(22) Filed: Nov. 19, 2004

(65) Prior Publication Data

US 2006/0122490 A1    Jun. 8, 2006

(51) Int. Cl.
*A61B 5/05* (2006.01)
(52) U.S. Cl. .................. 600/413; 600/407; 600/410; 600/509; 600/512
(58) Field of Classification Search ............ 600/407, 600/410, 413, 509, 512
See application file for complete search history.

(56) References Cited

U.S. PATENT DOCUMENTS

| | | | |
|---|---|---|---|
| 4,712,560 A | | 12/1987 | Schaefer et al. |
| 4,865,043 A | * | 9/1989 | Shimoni ............... 600/513 |
| 5,052,398 A | * | 10/1991 | Gober .................. 600/509 |
| 5,987,348 A | * | 11/1999 | Fischer et al. .......... 600/413 |
| 6,070,097 A | * | 5/2000 | Kreger et al. .......... 600/521 |
| 6,501,979 B1 | * | 12/2002 | Manning et al. ........ 600/413 |
| 2002/0188211 A1 | * | 12/2002 | Voith ................. 600/509 |
| 2003/0088174 A1 | * | 5/2003 | Sussman et al. ........ 600/410 |
| 2004/0073124 A1 | * | 4/2004 | Axel .................. 600/509 |

OTHER PUBLICATIONS

Jon M. Chia et al., Performance of QRS Detection for Cardiac Magnetic Resonance Imaging with a Novel Vectorcardiographic Triggering Method, Journal of Magnetic Resonance Imaging, 2000, pp. 678-688, vol. 12, Publisher: Wiley-Liss, Inc.
Ivan K. Daskalov et al., Developments in ECG Acquisition, Preprocessing, Parameter Measurement, and Recording, IEEE Engineering in Medicine and Biology, Mar./Apr. 1998, pp. 50-58, vol. 0739-5175, No. 98.
Stefan E. Fischer et al., Novel Real-Time R-Wave Detection Algorithm Based on the Vectorcardiogram for Accurate Gated Magnetic Resonance Acquisitions, Magnetic Resonance in Medicine, 1999, pp. 361-370, vol. 42, Publisher: Wiley-Liss, Inc.

* cited by examiner

*Primary Examiner*—Brian Casler
*Assistant Examiner*—James Kish
(74) *Attorney, Agent, or Firm*—Ziolkowski Patent Solutions Group, SC (57) ABSTRACT

A system and method for MR imaging is disclosed that includes an MRI system having a plurality of gradient coils positioned about a bore of a magnet to impress a polarizing magnetic field and an RF transceiver system and an RF switch controlled by a pulse module to transmit RF signals to an RF coil assembly to acquire MR images. A computer is included that is programed to generate a motion waveform from a physiological signal acquired from a subject to be imaged and compare a shape of the motion waveform to a shape of a reference motion waveform to identify points in the motion waveform corresponding to a periodic complex. The computer is also programed to trigger MR data acquisition from the subject upon identification of the periodic complex.

25 Claims, 4 Drawing Sheets

SYSTEM AND METHOD FOR IDENTIFYING PERIODIC MOTION COMPLEXES FOR MR IMAGING TRIGGERING

BACKGROUND OF THE INVENTION

The present invention relates generally to a magnetic resonance (MR) imaging and, more particularly, to a system and method for identifying periodic motion complexes for MR imaging triggering.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", MZ, may be rotated, or "tipped", into the x-y plane to produce a net transverse magnetic moment Mt. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Magnetic resonance imaging is a diagnostic imaging technique commonly used to review, identify, and diagnose pathologies or abnormalities in a scan subject, e.g., medical patient. For example, MR images of the cardiac region are often used by health care professionals to diagnose medical conditions. Traditional MR evaluations of the cardiac region often rely on repeated cardiac-gated acquisition of MR data in order to reduce image degradation resulting from the continuous movement of the cardiac region due to respiratory and/or circulatory physiological functions.

To achieve a cardiac-gated acquisition of MR data, systems have been developed that rely on detection of a particular point in the motion cycle as a trigger to repeatedly acquire data at approximately the same phase of the motion cycle. An electrocardiogram (ECG) is generally utilized to monitor the cardiac cycle and identify a particular peak, often an R-peak, within the ECG waveform. By identifying an occurrence of the R-peak, these systems infer that a Q-peak and S-peak are associated with the R-peak and thereby identify an occurrence of a QRS complex. The identification of a QRS complex is then used as a point for triggering the acquisition of MR data from the subject to be imaged.

However, the R-peak can often be distorted or obscured by strong noise associated with MR environments. For example, spikes may be induced within the ECG waveform by RF pulses or gradient pulses and may be misidentified as an R-peak. Accordingly, such systems may infer the spike as an R-pulse of a QRS complex and mistrigger imaging. Furthermore, abnormal patient conditions such as premature ventricular contraction (PVC) may hinder detection of an R-peak. Accordingly, many identification systems may cause imaging to be triggered prematurely or fail to trigger entirely thereby degrading the image quality and extending scan durations.

Accordingly, systems have been designed to review multiple features of the ECG feedback or Vectorcardiogram (VCG) feedback to provide an accurate detection of an R-peak. Specifically, some systems monitor an amplitude and a first derivative of the ECG waveform and assume that the R-peak will be the highest magnitude in the ECG waveform. Within these systems, the assumption that the R-peak will have the largest amplitude provides the fundamental basis for detection of the R-peak. However, this assumption also provides a primary basis for inaccuracies in detecting the R-peak and may lead to mistriggering or trigger lapses during gated MR processes.

That is, systems relying on amplitude and first derivative of the ECG waveform for detection of an R-peak may misinterpret artifacts or noise that have an amplitude larger than a given R-peak as an R-peak. Specifically, when a spike, T-Swell, or PVC are present, which have similar amplitude to the amplitude of a QRS complex, such amplitude-based systems may fail to identify R-peaks or erroneously identify R-peaks. For example, magnetohydrodyamic spikes may have a larger amplitude than an R-peak. These spikes may cause an amplitude-based triggering system to detect the spike as an R-peak and mistrigger data acquisition. Additionally, noise associated with the MR imaging process may cause the first derivative of the ECG waveform to be higher than that of the QRS complex and cause a mistrigger or trigger failure. As a result, both amplitude and first derivative based algorithms may result in poor image quality and require re-scanning of the subject.

It would therefore be desirable to have a system and method capable of accurately detecting a cyclical physiological point to trigger imaging in the presence of noise and artifacts. Specifically, it would be desirable to have a robust, reliable, and complete system for evaluating information within ECG or VCG waveforms to improve accuracy of triggered data acquisitions.

BRIEF DESCRIPTION OF THE INVENTION

The present invention provides a system and method of interactive MR imaging that overcomes the aforementioned drawbacks. The present invention provides a system and method to perform triggered MR data acquisitions based on periodic physiological motion of a subject to be imaged.

In accordance with one aspect of the invention, an MR imaging (MRI) apparatus is disclosed that includes an MRI system. The MRI system has a plurality of gradient coils positioned about a bore of a magnet to impress a polarizing magnetic field and an RF transceiver system and an RF switch controlled by a pulse module to transmit RF signals to an RF coil assembly to acquire MR images. A computer is included that is programmed to generate a motion waveform from a physiological signal acquired from a subject to be imaged and compare a shape of the motion waveform to a shape of a reference motion waveform to identify points in the motion waveform corresponding to a periodic complex. The computer is also programmed to trigger MR data acquisition from the subject upon identification of the periodic complex.

According to another aspect of the invention, a method of tracking physiological motion within a subject of an imaging data acquisition is disclosed. The method includes monitoring a physiological motion waveform of a subject to be imaged and comparing a shape of the physiological motion waveform and that of a reference physiological motion waveform. The method also includes identifying a periodic complex in the physiological motion waveform from the comparison and triggering acquisition of imaging data upon identifying the periodic complex.

In accordance with another aspect, the invention includes a computer readable storage medium having a program stored thereon that when executed by a processor causes the processor to identify a shape within a set of baseline cardiac waveforms indicative of a baseline QRS complex. The processor is also caused to quantify a baseline shape measure of the QRS complex and acquire a patient-specific cardiac waveform from a subject to be imaged. Further, the processor is caused to quantify a patient-specific shape measure from the patient-specific cardiac waveform, compare the quantified patient-specific shape measure to the baseline shape measure to identify a QRS complex in the patient-specific cardiac waveform, and trigger acquisition of imaging data from the subject upon identifying the QRS complex in the patient-specific cardiac waveform.

In accordance with yet another aspect of the invention, a computer readable storage medium is disclosed having a computer program stored thereon and representing a set of instructions that when executed by a computer causes the computer to monitor a motion signal acquired from a subject to be imaged. The computer is also caused to compare the motion signal to a trigger point indicator, identify a potential periodic event within the motion signal if at least a portion of the motion signal corresponds to the trigger point indicator, and, if the potential periodic event corresponds to an artifact in the motion signal, disregard the potential periodic event.

According to another aspect of the invention, a medical imaging device is disclosed that includes means for acquiring a signal indicative of physiological motion in a subject to be imaged and means for identifying points in the signal. The medical imaging device also includes means for determining a shape of a portion of the signal from the identified points and means for determining trigger points for an imaging data acquisition from the determined shape.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention provides a system and method to synchronize a gated MR data acquisition with physiological motion of a subject to be imaged.

Figure 1:
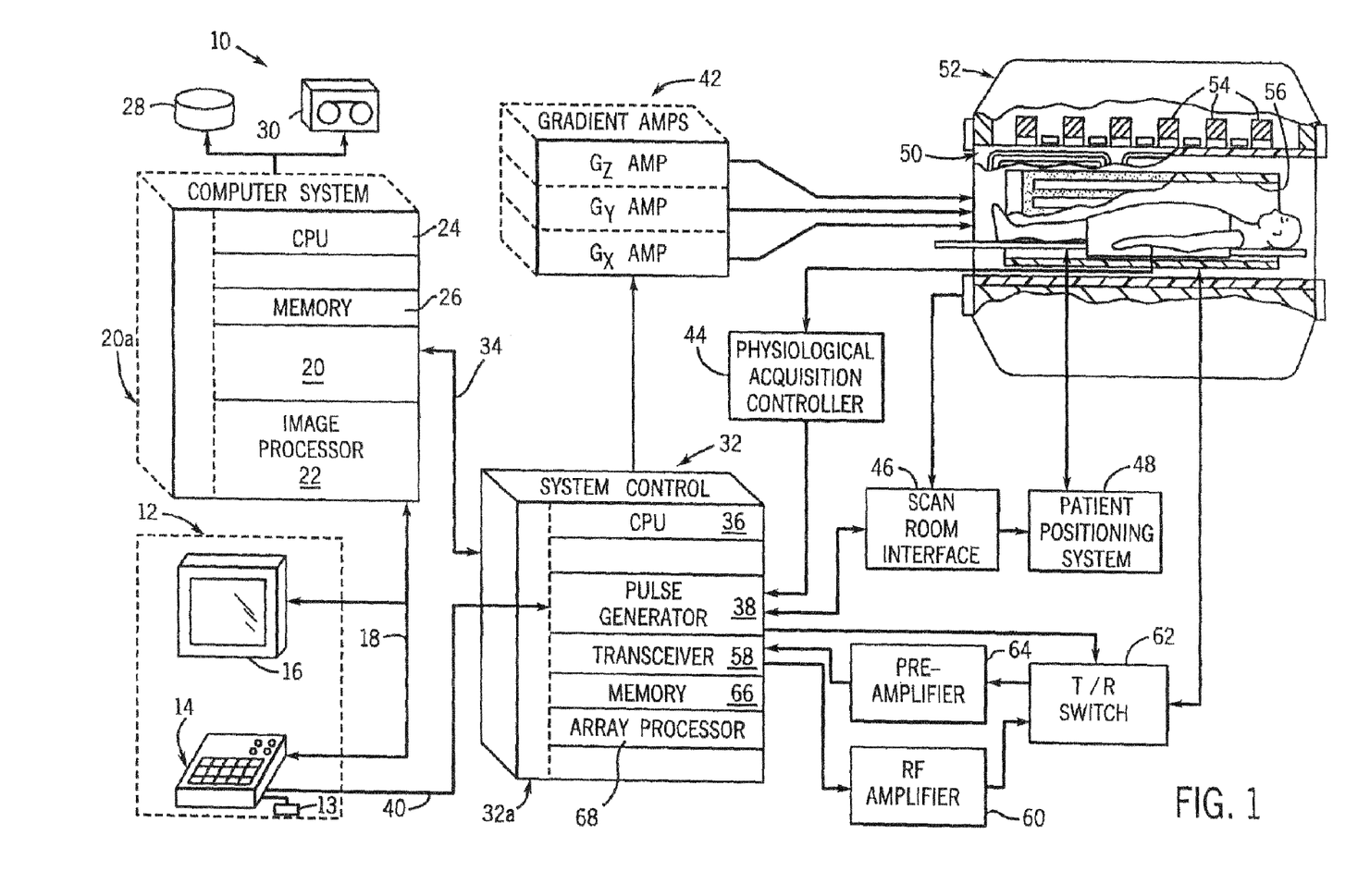
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a superconducting magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

Figure 2:
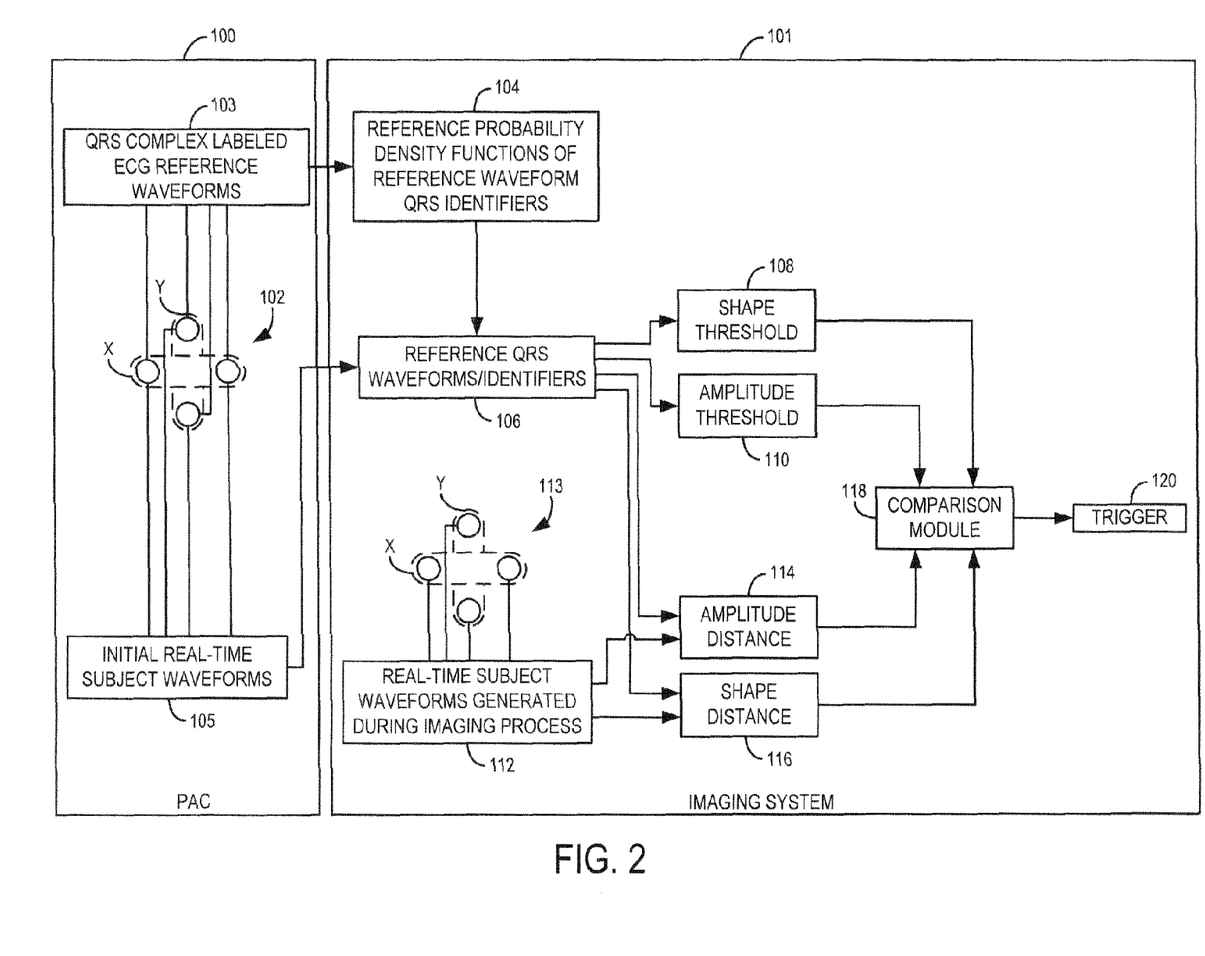
FIG. 2 is a block diagram illustrating a process flow for triggering data acquisition in accordance with the present invention.

Referring now to FIG. 2, a block diagram illustrating a process flow for triggering data acquisition is shown. A first portion of the process flow uses systems within a physiological acquisition controller (PAC) 100. The PAC 100 is utilized in an initialization stage for the acquisition of two distinct data sets prior to disposing the subject to be monitored within a medical imaging device 101. Specifically, the PAC 100 includes ECG leads 102 that are configured in two transverse groups labeled "X" and "Y." That is, the ECG leads 102 form an X lead set and a Y lead set that, as will be described, creates a convention for identifying trigger points within the derived ECG and/or VCG waveform.

As previously stated, two data sets are derived during initialization and while the subject is located externally from the imaging device 101. A first data set is derived using the ECG leads 102 to collect data sets from numerous individuals. By gathering this first set of waveforms externally from the imaging device 101, the derived waveforms do not include noise attributable to the imaging device 101 itself. Furthermore, by positioning the subject away from the imaging device, the subject is typically more relaxed, which may increase the accuracy and precision of the derived waveform.

These data sets are then compiled and labeled, as will be described with respect to FIGS. 3 and 4, to identify QRS complexes within the derived waveforms 103. The labeled waveforms are then stored as reference probability density functions 104. Specifically, probability distributions of the duration, amplitude, shape, and period of the QRS complexes are stored for use in later imaging of a subject. Accordingly, an a priori or reference data set including cardiac waveforms from various subjects is compiled, identified, labeled, and stored 104.

When a candidate or subject is identified for a particular imaging process, the PAC 100 is used to derive the second data set. Specifically, real-time cardiac waveforms 105 are acquired from a candidate or subject to be imaged. These initial subject waveforms 105 are again generated prior to positioning the subject in the bore of the imaging device so as not to introduce noise due to the imaging device and to ensure that the subject is in a relaxed state.

The initial subject waveforms 105 are then processed and combined with the stored reference probability density functions 104 to form reference QRS waveforms/identifiers 106. Specifically, the derived real-time candidate waveforms 105 are combined with the reference probability density functions 104 to compile reference QRS waveform/identifiers 106 that include data from the initial subject waveforms 104. The reference QRS waveform/identifiers 106 are then used to select a shape threshold 108 and amplitude threshold 110. It is contemplated that the shape threshold 108 and the amplitude threshold 110 may be user selected parameters or may be automatically selected based on the initial real-time subject waveforms 105. Once the shape threshold 108 and amplitude threshold 110 are selected for the imaging subject, the system is prepared for imaging. That is, as will be described with respect to FIGS. 3 and 4, the shape threshold 108 and amplitude threshold 110 are used to identify shape and amplitude features indicative of a cyclical trigger point in real-time subject waveforms derived during imaging of the subject 112.

At this time the initialization state is complete and the subject to be imaged is prepared for imaging. The subject is placed within the imaging device 101 where an ECG system 113 is utilized to acquire the real-time subject waveforms 112 during the ensuing imaging process. The subject waveforms 112 derived while the imaging subject is in the imaging device 101 along with the reference QRS waveforms/identifiers 106 are used to quantify a measure of amplitude distance 114 and shape distance 116. Specifically, as will be described with respect to FIGS. 3 and 4, the amplitude distance 114 is calculated and compared to the amplitude threshold 110 and the shape distance 116 is calculated compared to the shape threshold 108 by a comparison module 118 to determine whether a trigger 120 should be issued to initiate gated data acquisition.

In accordance with one embodiment, if both the shape distance 116 and the amplitude distance 114 are less than the corresponding thresholds 108, 110, a trigger 120 configured to initiate MR data acquisition is generated. However, due to the high accuracy of identifying the desired periodic motion complex, particularly the QRS complex, based on the shape distance 116 and shape threshold 108 comparison, it is contemplated that the triggering 120 may be solely or primarily based on the comparison of the shape distance 116 to the shape threshold 108. In this case, the evaluation of the amplitude distance 114 with respect to the amplitude threshold 110 may serve as a backup or secondary consideration for generating the trigger 120.

Figure 3:
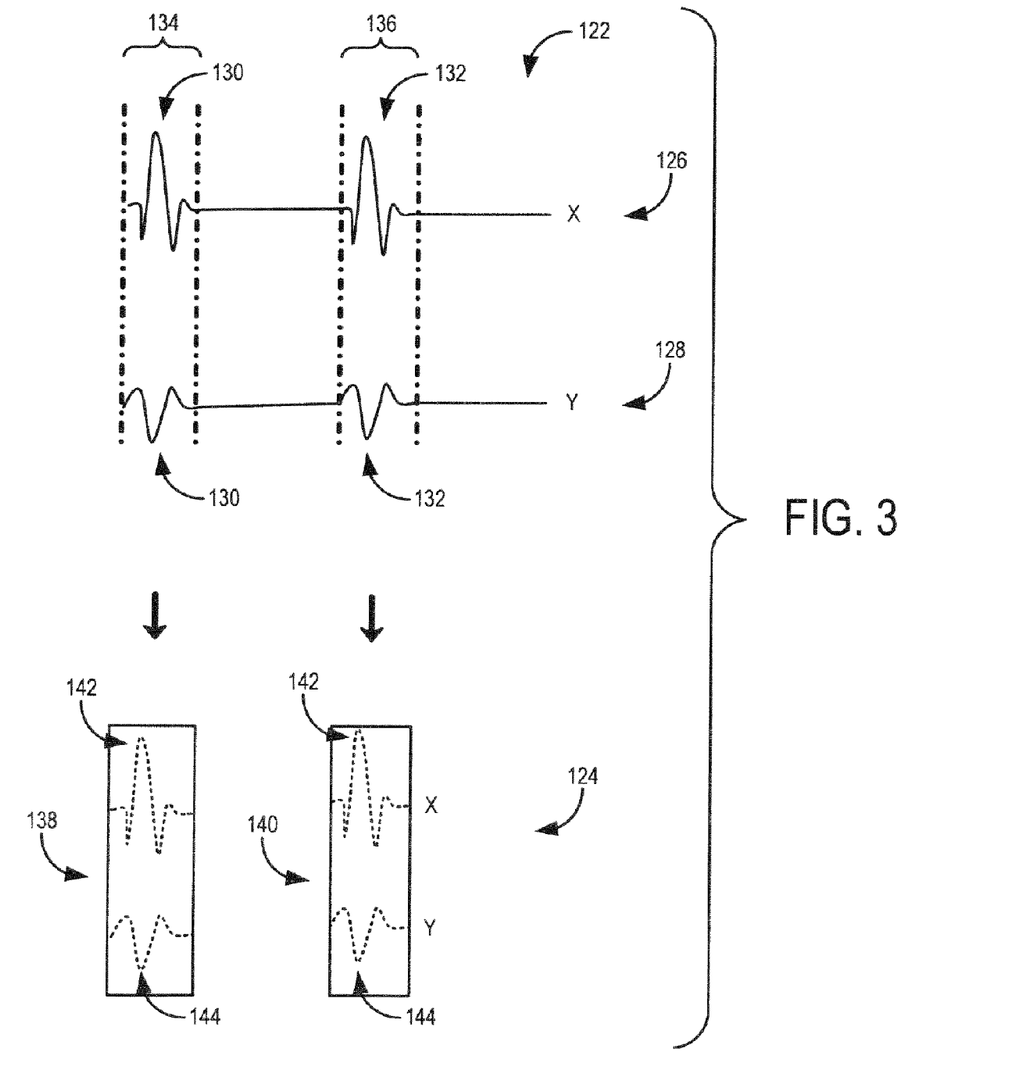
FIG. 3 is an illustration of an identified reference waveform in accordance with the present invention.

Referring now to FIG. 3, an example reference waveform 122 and corresponding reference peaks 124 are shown. Specifically, as described with respect to FIG. 2, baseline or reference waveforms 122 are generated using a cross configured ECG or VCG system. As such, a reference X waveform 126 corresponding to the X leads of the ECG or VCG system and a reference Y waveform 128 corresponding to the Y leads of the ECG or VCG system are derived. The system is configured to identify and label reference peak pairs 130, 132 corresponding to QRS complexes 134, 136 within the reference X waveform 126 and reference Y waveform 128. As will be described in detail, the distance between the reference peak pairs 130, 132 and amplitude distance between the reference peak pairs 130, 132 within the reference QRS complexes 134, 136 are used to identify an occurrence of QRS complexes in a subject waveform.

Once the QRS complexes 134, 136 within the reference waveforms 122 are identified and labeled as such, the data is stored as reference pairs of peaks 138, 140. Specifically, each pair of reference peaks 130, 132 includes a reference X peak 142 and a reference Y peak 144. Information for each pair of reference peaks 138, 140 including amplitude, duration, and period data is labeled and stored for comparison to subject waveforms to determine imaging trigger points.

Figure 4:
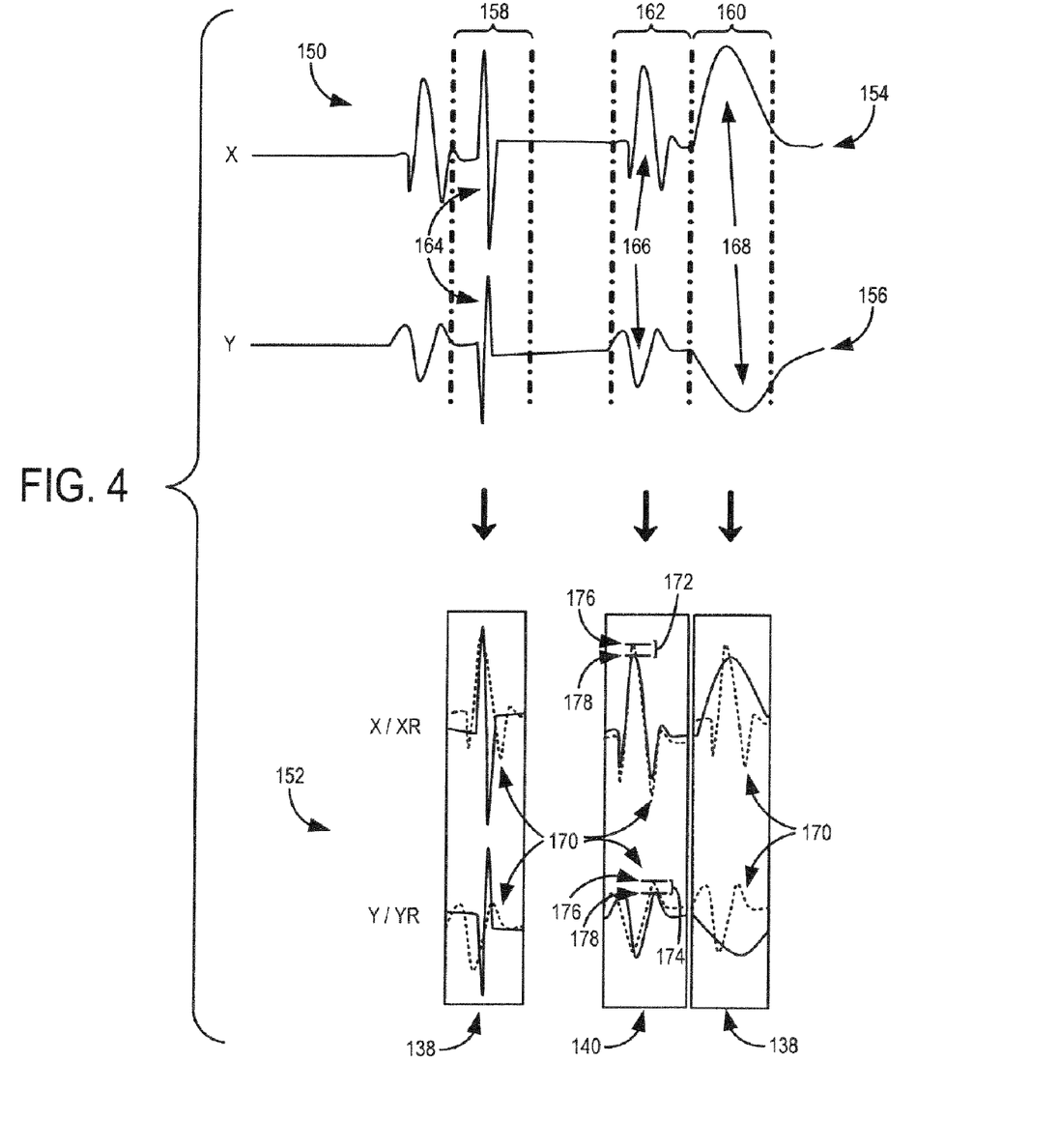
FIG. 4 is an illustration of a technique for evaluating a patient waveform in accordance with the present invention.

Referring now to FIG. 4, an exemplary subject waveform 150 and evaluation of the subject waveform against the reference peak pair 138, 140, derived as described with respect to FIG. 3, are shown as referenced with numeral 152. As described with respect to FIGS. 2 and 3, once reference waveforms are compiled, reference QRS complexes identified, and reference peak pairs labeled and identified, acquisition of a subject waveform 150 from a subject to be imaged may be commenced. Again, the ECG or VCG system is utilized to gather the subject waveform 150 including a subject X waveform 154 and a subject Y waveform 156. Unlike the reference waveforms 126, 128 of FIG. 3 that are gathered to compile reference peak pairs 138, 140, the subject X waveform 154 and subject Y waveform 156 are derived while the subject is within the imaging device. Accordingly, it is more likely that the subject X waveform 154 and subject Y waveform 156 may include artifacts or noise 158, 160 induced by the imaging system or due to increased stress levels of the subject. These artifacts or noise 158, 160 may surround a QRS complex 162 with the subject X waveform 154 and subject Y waveform 156 and obscure identification of the QRS complex 162.

Accordingly, as stated with respect to FIG. 2, the system is configured to determine a shape distance and amplitude distance of the subject waveform 150 and compare these distances to respective thresholds to identify the QRS complex 162 within the subject waveform 150 and trigger MR data acquisition. To this end, the system is configured to monitor a shape of the subject waveform 150 and identify peak pairs 164-168 within the subject waveform 150. That is, each peak pair includes one peak from within the subject X waveform 154 and one peak from within the subject Y waveform 156.

Upon detecting a peak pair 164-168 within the subject waveform 150, the system is configured to determine, in real-time or near real-time, the shape distance and amplitude distance of the peak pair 164-168 and compare the shape distance and amplitude to the reference peak pairs 138, 140. In accordance with one embodiment, the shape distance is quantified using an amplitude-delay-invariant minimum vector distance expression, where the vectors are pieces of fixed length within the subject waveforms 150.

In particular, the distance measure for the shape is calculated by:

$$\text{Distance\_shape}(X,Y) = \min_i(\|XR_i - X + a_i\| + \|YR_i - Y + b_i\|) \quad \text{Eqn. 1};$$

$$a_i = \text{sum}(XR_i - X)/\text{length}(X) \quad \text{Eqn. 2; and}$$

$$b_i = \text{sum}(YR_i - Y)/\text{length}(Y) \quad \text{Eqn. 3}.$$

$XR_i$ and $YR_i$ represent the $i^{th}$ reference pair of peaks 138, 140 of the reference waveforms 170 (shown in dashed lines) generated by the X leads and Y leads, respectively, of the cross-configured ECG system. Additionally, X and Y represent the subject pair of peaks 164-168 of the subject waveform 150 generated by the X leads and Y leads, respectively. Furthermore, $a_i$ represents the shift 172 in amplitude for the subject waveform 150 generated by the X leads and $b_i$ represents the shift in amplitude 174 of subject waveform 150 generated by the Y leads. The term $\|XR_i - X\|$ represents the vector distance between the reference waveform 170 and the subject waveform 150 generated by the X leads as calculated by:

$$\|\blacksquare\| = SQRT((XR_1 - X_1)^2 + (XR_2 - X_2)^2 + \ldots + (XR_n - X_n)^2) \quad \text{Eqn. 4}.$$

The term $\|YR_i - Y\|$ represents the vector distance between the reference waveform 170 and the subject waveform 150 generated by the Y leads as calculated by:

$$\|\blacksquare\| = SQRT((YR_1 - Y_1)^2 + (YR_2 - Y_2)^2 + \ldots + (YR_n - Y_n)^2) \quad \text{Eqn. 5}.$$

The amplitude similarity is quantified by the distance of peaks 164-168 within the subject waveform 150 to peaks in the reference waveforms 170. Accordingly, the amplitude distance is calculated by:

$$\text{Distance\_amplitude}(X,Y) = SQRT((AX - AX0_i)^2 + (AY - AY0_i)^2) \quad \text{Eqn. 6}.$$

$AXO_i$ and $AYO_i$ represent the $i^{th}$ reference pair of peak amplitudes 176 within the reference waveforms 170 generated by the X leads and the Y leads, respectively, of the cross-configured ECG system. Additionally, AX and AY represent the patient pair of peak amplitudes 178 within the subject waveforms 150 generated by the X leads and the Y leads, respectively.

Accordingly, when the shape and the amplitude of the subject X waveform 154 and subject Y waveform 156 are compared to the reference waveform 170, the QRS complex 162 within the subject waveforms 154, 156 and corresponding peaks 166 substantially align with the reference peak pairs 140 and are readily distinguishable from peaks attributable to artifacts and noise 158, 160 when compared to the reference peak pairs 138. That is, since the shape of the subject QRS complex 162 is relatively stable, less affected by subject breath and motion, and substantially differs from the shape of a spike, T-Swell, or PVC, upon considering shape rather than just amplitude alone, the subject QRS complex 162 can be readily distinguished from artifacts and noise 158, 160. Furthermore, by using the shape feature of the ECG or VCG subject X and Y waveforms 154, 156, the accuracy of human observer differentiation of the subject QRS complex 162 from noisy false peaks 158, 160 is greatly increased. Additionally, by utilizing the shape of the ECG or VCG subject waveforms 154, 156 rather than just a single identifier, such as amplitude, for detection, an increased number of data points are considered and, therefore, the signal energy and the SNR are increased.

The technique may be utilized to automate gating and reduce the requirements placed upon an operator of the imaging device. That is, the system first acquires ECG/VCG waveforms. The system then automatically determines the polarity of the leads and the threshold level, analyzes the ECG/VCG waveforms to identify QRS complexes within the ECG/VCG waveforms, and triggers data acquision.

Therefore, the utilization of the a priori amplitude, duration, and period information of the QRS complex across various subjects to form a reference to identify shape and amplitude features of the QRS complex for a specific subject greatly improves the performance of cardiac triggering over previous methods such as those that only use maximum amplitude and/or maximum derivative of the signal to perform triggering. Specifically, by using an amplitude-delay-invariant expression to measure the similarity between candidate peaks and reference peaks, the shape of the QRS complex can be readily distinguished from artifacts, noise, and the like. Furthermore, the technique decreases sensitivity to motion artifacts that reduce SNR and may cause false triggering at spikes, T Swells, and PVCs within the ECG and/or VCG data.

While the above-described invention was described with respect to cardiac gating of MR data acquisition, the technique is readily applicable to other electrical signals of interest in MR, such as respiratory gating. Furthermore, though described with respect to MR environments, the above-described technique is also applicable to other systems where monitoring of physiological signals from a patient, particularly within a noisy environment, is desirable including, but not limited to CT, PET, SPECT, ultrasound, x-ray, and the like.

Therefore, the present invention includes an MR imaging (MRI) apparatus. The MRI apparatus includes an MRI system having a plurality of gradient coils positioned about a bore of a magnet to impress a polarizing magnetic field and an RF transceiver system and an RF switch controlled by a pulse module to transmit RF signals to an RF coil assembly to acquire MR images. A computer is included that is programmed to generate a motion waveform from a physiological signal acquired from a subject to be imaged and compare a shape of the motion waveform to a shape of a reference motion waveform to identify points in the motion waveform corresponding to a periodic complex. The computer is also programmed to trigger MR data acquisition from the subject upon identification of the periodic complex.

In another embodiment of the present invention, a method of tracking physiological motion within a subject of an imaging data acquisition includes monitoring a physiological motion waveform of a subject to be imaged and comparing a shape of the physiological motion waveform and that of a reference physiological motion waveform. The method also includes identifying a periodic complex in the physiological motion waveform from the comparison and triggering acquisition of imaging data upon identifying the periodic complex.

Another embodiment of the present invention includes a computer readable storage medium that has a program stored thereon. When the program is executed by a processor, the program causes the processor to identify a shape within a set of baseline cardiac waveforms indicative of a baseline QRS complex. The processor is also caused to quantify a baseline shape measure of the QRS complex and acquire a patient-specific cardiac waveform from a subject to be imaged. Further, the processor is caused to quantify a patient-specific shape measure from the patient-specific cardiac waveform, compare the quantified patient-specific shape measure to the baseline shape measure to identify a QRS complex in the patient-specific cardiac waveform, and trigger acquisition of imaging data from the subject upon identifying the QRS complex in the patient-specific cardiac waveform.

A further embodiment of the present invention has a computer readable storage medium that includes a computer program stored thereon. The computer program represents a set of instructions that when executed by a computer causes the computer to monitor a motion signal acquired from a subject to be imaged. The computer is also caused to compare the motion signal to a trigger point indicator, identify a potential periodic event within the motion signal if at least a portion of the motion signal corresponds to the trigger point indicator, and, if the potential periodic event corresponds to an artifact in the motion signal, disregard the potential periodic event.

According to another embodiment of the invention, a medical imaging device includes means for acquiring a signal indicative of physiological motion in a subject to be imaged and means for identifying points in the signal. The medical imaging device also includes means for determining a shape of a portion of the signal from the identified points and means for determining trigger points for an imaging data acquisition from the determined shape.

The present invention has been described in terms of the preferred embodiment, and it is recognized that equivalents, alternatives, and modifications, aside from those expressly stated, are possible and within the scope of the appending claims.

What is claimed is:

1. An MR imaging (MRI) apparatus comprising:
    an MRI system having a plurality of gradient coils positioned about a bore of a magnet to impress a polarizing magnetic field and an RF transceiver system and an RF switch controlled by a pulse module to transmit RF signals to an RF coil assembly to acquire MR images; and
    a computer programmed to:
        generate a first data set from a first physiologic signal generated via a first cardiac lead associated with a subject and from a second physiologic signal generated via a second cardiac lead associated with the subject and non-aligned with the first cardiac lead, wherein the first data set represents a first cardiac event;
        generate a second data set from the first and second physiologic signals, wherein the second data set represents a second cardiac event;
        generate a third data set from a pair of cardiac signals, wherein the pair of cardiac signals are generated via the first and second cardiac leads, and wherein the third data set represents a potential cardiac event of the subject;
        determine a first comparison value based on the first data set and the third data set;
        determine a second comparison value based on the second data set and the third data set; and
        trigger an image acquisition based on a lesser of the first and second comparison values.

2. The method of claim 1 wherein the lesser of the first and second comparison values is determined by a relationship that comprises:

Lesser Value=$\min_i(\|XR_i-X+a_i\|+\|YR_i-Y+b_i\|)$, with $a_i$=sum($XR_i-X$)/length($X$), and $b_i$=sum($YR_i-Y$)/length($Y$), where $XR_i$ represents a first peak in the first physiologic signal in a first iteration and a second peak in the first physiologic signal in a second iteration, $YR_i$ represents a first peak in the second physiologic signal in the first iteration and a second peak in the second physiologic signal in the second iteration, X represents a peak in a first cardiac signal of the pair of cardiac signals, and Y represents a peak in a second cardiac signal of the pair of cardiac signals.

3. The MRI apparatus of claim 1 wherein the computer is further programmed to compare the first and second comparison values to a threshold value, wherein the lesser of the first and second comparison values is less than the threshold value.

4. The MRI apparatus of claim 1 wherein the generation of the first and second data sets is further based on a set of functions derived from data from a plurality of individuals other than the subject.

5. The MRI apparatus of claim 4 wherein the set of functions is a set of probability of density functions based on at least one of a QRS complex amplitude, a QRS complex duration, and a QRS complex period.

6. The MRI apparatus of claim 1 wherein the first data set comprises data representing a first cardiac waveform shape generated via the first cardiac lead and representing a second cardiac waveform shape generated via the second cardiac lead, wherein the first and second cardiac waveforms represent the first cardiac event.

7. The MRI apparatus of claim 6 wherein the third data set comprises data representing a first potential cardiac waveform generated via the first cardiac lead and representing a second potential cardiac waveform generated via the second cardiac lead, wherein the first and second potential cardiac waveforms represent the potential cardiac event.

8. The MRI apparatus of claim 7 wherein the computer is further programmed to:
    determine a first vector distance between the first cardiac waveform and the first potential cardiac waveform; and
    determine a second vector distance between the second cardiac waveform and the second potential cardiac waveform, wherein the first comparison value is based on the first and second vector distances.

9. The MRI apparatus of claim 1 wherein the first and second cardiac leads are determined by one of an electrocardiogram apparatus and a vectorcardiogram apparatus.

10. The MRI apparatus of claim 1 wherein the first and second physiologic signals are generated externally from the MRI apparatus and wherein the pair of cardiac signals are generated within a magnetic field of the MRI apparatus.

11. A computer readable storage medium having a program stored thereon that when executed by a processor causes the processor to:
- identify a first waveform shape and a second waveform shape respectively from a first cardiac signal and a second cardiac signal from a subject, wherein the first and second waveform shapes represent a first QRS cardiac event, wherein the first cardiac signal is generated via a first cardiac lead and wherein the second cardiac signal is generated via a second cardiac lead non-aligned with the first cardiac lead;
- identify a third waveform shape and a fourth waveform shape respectively from the first and second cardiac signals, wherein the third and fourth waveform shapes represent a second QRS cardiac event, wherein identification of the first, second, third, and fourth waveform shapes is based on at least one function derived from cardiac data acquired from a plurality of individuals other than the subject;
- identify a fifth waveform shape and a sixth waveform shape from a pair of cardiac signals generated via the first and second cardiac leads, wherein the fifth and sixth waveform shapes represent a third QRS cardiac event;
- determine a first shape value based on the first and second waveform shapes and based on the fifth and sixth waveform shapes;
- determine a second shape value based on the third and fourth waveform shapes and based on the fifth and sixth waveform shapes; and
- trigger acquisition of imaging data from the subject based on a lesser of the first shape value and the second shape value.

12. The method of claim 11 wherein the lesser of the first and second shape values is determined by a relationship that comprises:

$$\text{Min\_Distance\_shape}(X,Y) = \min_i(\|XR_i - X + a_i\| + \|YR_i - Y + b_i\|),$$

with $a_i = \text{sum}(XR_i - X)/\text{length}(X)$, and $b_i = \text{sum}(YR_i - Y)/\text{length}(Y)$, where $XR_i$ represents a peak of the first waveform shape in a first iteration and a peak of the third waveform in a second iteration, $YR_i$ represents a peak of the second waveform in the first iteration and a peak of the fourth waveform shape in the second iteration, X represents a peak of the fifth waveform shape, and Y represents a peak of the sixth waveform shape.

13. The computer readable storage medium of claim 11 wherein the at least one function comprises a probability of density function based on at least one of QRS amplitudes, QRS durations, and QRS periods of the plurality of individuals.

14. The computer readable storage medium of claim 11 wherein the program further causes the processor to compare each of the first and second shape values to a first threshold to ensure that each of the first and second shape values do not exceed the first threshold.

15. The computer readable storage medium of claim 11 wherein the determination of the first shape value is based on a first vector distance between the first waveform shape and the fifth waveform shape and based on a second vector distance between the second waveform shape and the sixth waveform shape.

16. The computer readable storage medium of claim 11 wherein the program further causes the processor to determine an amplitude value based on a change in amplitude between the first and fifth waveform shape and based on a change in amplitude between the second and sixth waveform shape, wherein the trigger of acquisition of the imaging data is further based on the amplitude value.

17. The computer readable storage medium of claim 16 wherein the program further causes the processor to compare the amplitude value to a threshold amplitude value.

18. The computer readable storage medium of claim 11 wherein the program further causes the processor to apply an amplitude-delay-invariant expression to determine the first and second waveform shape values.

19. The computer readable storage medium of claim 11 wherein the program further causes the processor to reconstruct an MR image from the imaging data.

20. A method of acquiring imaging data comprising:
- identifying a plurality of QRS reference waveform pairs associated with a subject and generated via a first cardiac lead and via a second cardiac lead non-aligned with the first cardiac lead, wherein each pair of the plurality of reference QRS waveform pairs represents a unique cardiac event such that a plurality of cardiac events are respectively represented by the plurality of reference waveform pairs, and wherein identifying a plurality of reference waveform pairs is based on cardiac data acquired from a plurality of individuals;
- monitoring a first physiological signal and a second physiological signal of the subject during an imaging procedure, wherein the first and second physiological signals are acquired via the first cardiac lead and the second cardiac lead, respectively;
- identifying a potential QRS waveform pair in the first and second physiological signals, wherein the potential QRS waveform pair represents one potential cardiac event;
- producing a plurality of comparison values respectively based on the plurality of QRS reference waveform pairs, wherein each correlation value of the plurality of correlation values is further based on the potential QRS waveform pair;
- identifying a minimum comparison value from the plurality of comparison values;
- triggering acquisition of imaging data based on the minimum comparison value; and
- reconstructing an image based on the acquired imaging data.

21. The method of claim 20 wherein identifying the minimum comparison value comprises implementing a relationship comprising:

$$\text{Min\_Distance\_shape}(X,Y) = \min_i(\|XR_i - X + a_i\| + \|YR_i - Y + b_i\|),$$

with $a_i = \text{sum}(XR_i - X)/\text{length}(X)$, and $b_i = \text{sum}(YR_i - Y)/\text{length}(Y)$, wherein each $XR_i$ represents a unique peak in the plurality of QRS reference waveform pairs and is associated with the first cardiac lead, each $YR_i$ represents a unique peak in the plurality of QRS reference waveform pairs and is associated with the second cardiac lead, X represents a peak of the potential QRS waveform pair corresponding to the first physiological signal, and Y represents a peak of the potential QRS waveform pair corresponding to the second physiological signal.

22. The method of claim 20 further comprising comparing the minimum comparison value to a first threshold value, wherein the minimum comparison value does not exceed the first threshold value.

23. The method of claim 20 wherein identifying the minimum correlation value comprises:
    determining a first vector distance between a first QRS reference waveform pair of the plurality of QRS reference waveform pairs and the potential QRS waveform pair, wherein the first vector distance is based on a first reference physiological signal generated via the first cardiac lead; and
    determining a second vector distance between the first QRS reference waveform and the potential QRS waveform pair, wherein the second vector distance is based on a second physiological signal generated via the second cardiac lead.

24. The method of claim 20 further comprising determining an amplitude value comprising:
    determining a first amplitude distance between one QRS reference waveform pair of the plurality of QRS reference waveform pairs and the potential QRS waveform pair, wherein the first amplitude distance is based on a first reference physiological signal generated via the first cardiac lead; and
    determining a second amplitude distance between the one QRS reference pair and the potential QRS waveform pair, wherein the second amplitude distance is based on a second reference physiological signal generated via the second cardiac lead.

25. The method of claim 24 wherein triggering acquisition of imaging data comprises triggering acquisition of imaging data based on the amplitude value.

* * * * *